United States Patent [19]

Foguet et al.

[11] Patent Number: 4,610,998
[45] Date of Patent: Sep. 9, 1986

[54] IMIDAZOLYLETHOXYINDANES AND USE AS ANTITHROMBOTIC AGENTS

[75] Inventors: Rafael Foguet; Ernesto Forne; Jose A. Ortiz; Aurelio Sacristan; Jose M. Castello, all of Barcelona, Spain

[73] Assignee: Ferrer Internacional, S.A., Barcelona, Spain

[21] Appl. No.: 807,432

[22] Filed: Dec. 9, 1985

[30] Foreign Application Priority Data

Dec. 10, 1984 [ES] Spain ............................ 539.074

[51] Int. Cl.⁴ .................. C07D 233/54; A61K 31/415
[52] U.S. Cl. ...................................... 514/399; 548/341
[58] Field of Search ........................ 548/341; 514/399

[56] References Cited

FOREIGN PATENT DOCUMENTS 2038821  7/1980  United Kingdom ............... 548/341

Primary Examiner—Henry R. Jiles
Assistant Examiner—Robert C. Whittenbaugh
Attorney, Agent, or Firm—Michael J. Striker

[57] ABSTRACT

The invention is concerned with the novel imidazolylethoxy indanes represented by formula (I),

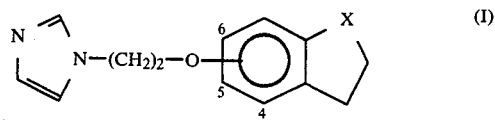

or a pharmacologically-acceptable salt thereof, a process for the preparation of them, and a pharmaceutical composition which contains these new compounds as active ingredient and can be used as antithrombotic and platelet antiaggregating agents.

12 Claims, No Drawings

IMIDAZOLYLETHOXYINDANES AND USE AS ANTITHROMBOTIC AGENTS

BACKGROUND OF THE INVENTION

The present invention relates to novel imidazolylethoxyindanes which have an effective antithrombotic activity, its pharmacologically-acceptable salts, and process for preparing the same.

More particularly, the present invention relates to novel imidazolylethoxyindanes represented by the general formula (I),

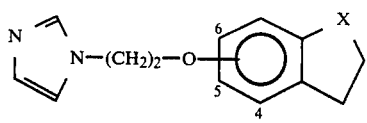

(I)

wherein X is a C=O group, a CH—CN group or a CH—COOH group, and the ether group (—O—) is bonded to the indanic group in the 4-, 5- or 6-position thereof, its pharmacologically-acceptable salts and process for preparing the same.

FIELD OF THE INVENTION

U.K. Pat. No. 2,038,821 discloses, among other compounds, 4-[2-(1H-imidazol-1-yl)ethoxy]benzoic acid (Dazoxiben) represented by the formula (A),

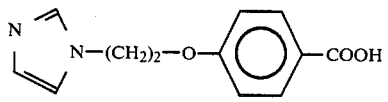

(A)

Dazoxiben belongs to an interesting group of antithrombotic imidazoles which are characterised by their ability to selectively inhibit the thromboxane synthetase enzyme without significantly inhibiting the prostacyclin formation unlike conventional antithrombotic drugs, such as acetylsalicylic acid (B),

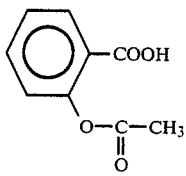

(B)

However, the clinical use of Dazoxiben does not seem to be a decisive therapy for thrombotic diseases.

SUMMARY OF THE INVENTION

The present inventors studied therefore for finding out a more effective antithrombotic agent, and discovered that the compounds represented by the above-mentioned formula (I) showed, in addition to an important protection against mortality and respiratory distress induced by sodium arachiodonate which is evident for thrombosane synthetase imidazone inhibitors, an exceptional ability to inhibit the formation of thrombi by a physiological agent, adenosine diphosphate (ADP), and surpasses the action of Dazoxiben.

The present invention is based on this finding.

DETAILED DESCRIPTION OF THE INVENTION

Pharmacologically-acceptable salts of the compounds having the said formula (I) are acid addition salts. Acid addition salts include mineral acid salts such as hydrochloride, sulfate, nitrate, hydrobromide, hydroiodide, phosphate, etc.; or organic acid salts such as acetate, maleate, fumarate, citrate or tartarate, etc.

Non-limiting examples of the compounds of this invention include:

(1) 5-[$\beta$-(1H-Imidazol-1-yl)ethoxy]-1-indanone
(2) 1-Cyano-5-[$\beta$-(1H-imidazol-1-yl)ethoxy]indane
(3) 5-[$\beta$-(1H-Imidazol-1-yl)ethoxy]indan-1-carboxylic acid hydrochloride
(4) 4-$\beta$-(1H-Imidazol-1-yl)ethoxy]-1-indanone
(5) 1-Cyano-4-[$\beta$-(1H-Imidazol-1-yl)ethoxy[indane
(6) 4-[$\beta$-(1H-Imidazol-1-yl)ethoxy]indan-1-carboxylic acid hydrochloride
(7) 6-[$\beta$-(1H-Imidazol-1-yl)ethoxy]-1-indanone
(8) 1-Cyano-6-[$\beta$-(1H-imidazol-1-yl)ethoxy]indane
(9) 6-[$\beta$-(1H-Imidazol-1-yl)ethoxy]indan-1-carboxylic acid hydrochloride According to the present invention the novel compounds, imidazolylethoxyindanes, represented by the general formula (I) can be prepared by the following method:

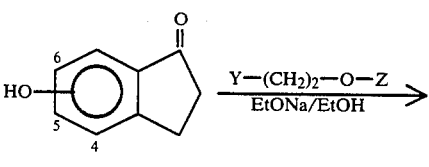

(II)

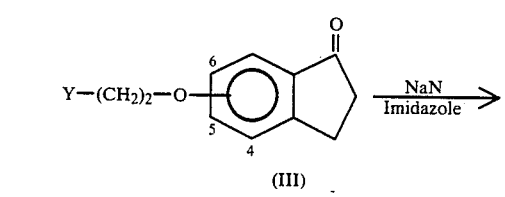

(III)

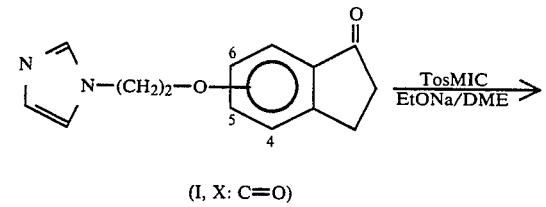

(I, X: C=O)

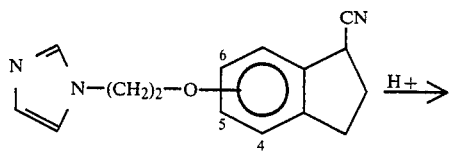

(I, X: CH—CN)

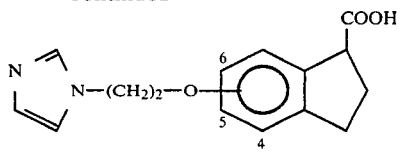

(I, X: CH—COOH)

TosMIC: (p-toluenesulfonyl)methylisocyanide
DME: dimethoxyethane

The hydroxylated indanones of general formula (II) are subjected to alkylation with a reagent of general formula Y-(CH$_2$)$_2$-O-Z, wherein Y is an halogen atom selected from chlorine or bromine, and Z is a migrant group selected from alkylsulfonyl or arylsulfonyl groups. The applicants have found out that this reaction conveniently occurs when Y is chlorine and Z is a p-toluensulfonyl group, in a strong basic medium preferably an alkaline alcoxide dissolved in an alcohol having 4 carbon atoms at most, such as sodium ethoxide, and at the boiling temperature of the mixture. In addition to Y=chlorine and Z=p-toluenesulfonyl, other groups are also preferred, namely, Y=bromine and Z=ethanesulfonyl, methanesulfonyl, benzenesulfonyl and the like.

The alkylation of imidazole with haloethoxide-indanones of the general formula (III), prepared as above described, occurs in the presence of a base strong enough as to ionize the imidazole molecule; alkaline hydrides, preferably sodium hydride, are suitable for this purpose. The reaction procedure requires an inert and aprotic solvent, preferably N,N-dimethylformamide, and a suitable temperature ranging from 60° C. to the boiling point of the mixture.

The so obtained imidazolylethoxyindanones of general formula (I, X: C=O) are subject to react with (p-toluenesulfonyl)methyl-isocyanide in a ether-like solvent, preferably dimethoxyethane, and in the presence of a strong base, preferably an alkaline alcoxide dissolved in an alcohol having 4 carbon atoms at most, such as sodium ethoxide in ethanol, and at a temperature ranging from −10° to 40° C. Thus, the carbonitriles of general formula (I, X: CH—CN) are obtained.

Then, the acid hydrolysis of the carbonitriles prepared as above described, preferably at boiling temperature of the mixture, leads to the respective acids of general formula (I, X: CH—COOH).

The reaction of the compounds of general formula (I) with acids leads to respective addition salts, being hydrochlorides preferred. Suitable solvents for the preparation of these salts are, for instance, water, acetone, alcohols having 4 carbon atoms at most or a mixture thereof.

The starting hydroxylated indanones (II) may be prepared according to either conventional methods in Organic Chemistry or specific procedures disclosed in the literature. Consequently, 5-hydroxy-1-indanone was prepared by demethylation of 5-methoxy-1-indanone (commercially available) with aluminum bromide dissolved in dry methylene chloride under reflux (Example 13):

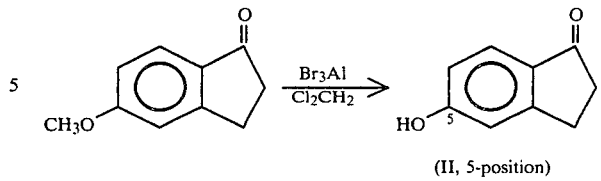

(II, 5-position)

In contrast, 4-hydroxy-1-indanone was prepared from coumarin (commercially available) by hydrogenation followed by internal Friedel-Craft's reaction (Rev.Soc.-Quim.Mex., 11, 39, 1967; Ni-Raney preparation: J.Org.-Chem., 26, 1625, 1961):

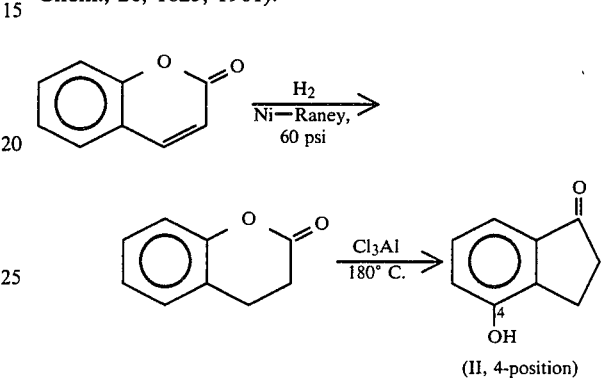

(II, 4-position)

6-Hydroxy-1-indanone was prepared from 3-(4-methoxyphenyl)propionic acid (commercially available) by internal Friedel-Crafts' reaction (J.Am.Chem.Soc., 67, 1853, 1945) followed by demethylation with aluminum bromide dissolved in benzene under reflux (U.S. Pat. No. 2,820,817):

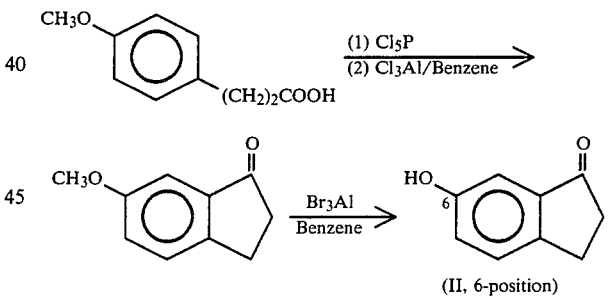

(II, 6-position)

ANTITHROMBOTIC ACTIVITY

The compounds of the present invention have an effective antithrombotic activity as evidenced by their protective action against mortality and respiratory distress induced by endovenous sodium arachidonate in mice (Kohler C. et al: Thrombosis Research, 9, 67–80, 1976). It was observed in this test the specific activity of 5-[β(1H-imidazol-1-yl)ethoxy]-indan-1-carboxylic acid hydrochloride showing 13.3 mg/kg DE$_{50}$ orally. Moreover, these compounds inhibit the in vitro platelet aggregation induced by ADP at 10 μM concentration in rat's richly-platelet plasma. Under these conditions, the IC$_{50}$ of 5-[β-(1H-imidazol-1-yl)ethoxy]indan-1-carboxylic acid is 2.5–5×10$^{-4}$M. On the other hand, when used ADP, as an aggregating agent, at a concentration of 2.5 μM in total blood of rats in vitro, an IC$_{50}$ of 7.1×10$^{-4}$M was obtained for 5-[β-(1H-imidazol-1-yl)e- thoxy]indan-1-carboxylic acid while Dazoxiben HCl at this concentration only caused a 30% inhibition.

Upon consideration of these properties, the compounds of this invention are useful agents in the treatment of cardiovascular diseases, such as thrombosis, coronary contractions, arrhythmias, ischaemic cerebral attack, migraine, myocardial infarction, angina pectoris and hypertension; repiratory disorders, e.g. asthma and apnea; and inflammatory conditions of organs and limbs. These compounds, due to their antithrombotic properties, reduce metastasis in a large number of tumors.

The compounds of the present invention mixed with pharmaceutically acceptable carriers can be administered by the oral route in the form of tablets, capsules, coated tablets, syrups, solutions, etc., by injectable route and by rectal route at daily doses ranging from 0.01 to 200 mg/kg.

The novel features which are considered characteristic of the invention are set forth in particular in the appended claims. The invention itself, however, both as to its construction and its method of operation, together with additional objects and advantages thereof, will best understood from the following description of specific embodiments.

DESCRIPTION OF THE PREFERRED EMBODIMENTS

EXAMPLE 1

5-(β-Chloroethoxy)-1-indanone

To a solution of sodium ethoxide in ethanol prepared from 5.68 g of sodium and 500 ml of absolute ethanol, 36.75 g of 5-hydroxy-1-indanone in 500 ml of slightly-heated ethanol are added in the course of 30 minutes. Then, 74.5 g of β-chloroethyl p-toluenesulphonate in 100 ml of ethanol are dropwise added, and the mixture is refluxed under stirring for 25 hours. Then the mixture is cooled, the insolubilized sodium p-toluenesulphonate 40 g, dry) is filtered off, and the ethanol is evaporated till dryness under vacuum. The residue (71.6 g) is treated with water (250 ml) and methylene chloride (250 ml); the aqueous phase is extracted two further times with methylene chloride, and the organic extracts are washed twice with 100 ml of 10% sodium hydroxide and with water till neutralization. The solvent is evaporated and the residue (54 g) is purified over silica-gel column; by eluting with methylene chloride:hexane (9:1) the excess β-chloro-ethyl p-toluenesulphonate is separated, and the desired product is isolated with methylene chloride; 26.6 g (51%) of a yellow solid are obtained. M.P. 79°-82° C. and analysis correct.

IR Spectrum (KBr), cm$^{-1}$: 3000–2900, 1695, 1600, 1250, 1090, 830.

$^1$H-NMR Spectrum (CDCl$_3$), ppm: 2.60 (m, 2H; —CH$_2$—CO—), 3.10 (m, 2H; Ar—CH$_2$—), 3.81 (t, 2H, J=6 Hz; —CH$_2$—O—), 4.30 (t, 2H, J=6 Hz; —CH$_2$Cl), 6.91 (m, 2H; Ar—) and 7.67 (d, 1H, J=9 Hz; Ar—).

EXAMPLE 2

5-[β-(1H-Imidazol-1-yl)ethoxy]-1-indanone

To 5.8 g of sodium hydride (55%) in paraffin, washed with benzene for removing this contaminant, 25 ml of dry N,N-dimethyl-formamide (DMF) are added and under stirring a solution of 8.23 g of imidazole in 35 ml of DMF is dropwise added; the mixture is heated at 100° C. for 1 hour, cooled and 25.48 g of 5-(β-chloro-ethoxy)-1-indanone in 155 ml of DMF are added, then heated again at 100°-110° C. for 3.5 hours. The mixture is cooled, 60 ml of ethanol are added and the solvents are concentrated till dryness at vacuum. The residue is taken in 200 ml of water under stirring, filtered off and treated again in the same manner. Once dried, it is filtered through a silica-gel column in chloroform:methanol (95:5) thus yielding, after evaporation, 20.50 g (70%) of white solid; M.P. 159°-161° C. and elemental analysis correct.

IR Spectrum (KBr), cm$^{-1}$: 3120–2900, 1690, 1590, 1250, 1050, 810, 770.

$^1$H-NMR (CDCl$_3$), ppm: 2.60 (m, 2H; —CH$_2$—CO—), 3.08 (m, 2H; Ar—CH$_2$—) 4.32 (s, wide, 4H; —CH$_2$—CH$_2$—O—), 6.75–7.1 and 7.5–7.75 (multiple bands, 5H, Ar—, Imidazole).

EXAMPLE 3

1-Cyano-5-[β-(1H-imidazol-1-yl)ethoxy]indane

To 15.2 g of 5-[β-(1H-imidazol-1-yl)ethoxy]-1-indanone and 18.78 g of (p-toluenesulfonyl)methylisocyanide in 450 ml of dimethoxyethane (DME), cooled at −5° C., a solution of sodium ethoxide in ethanol and dimethoxyethane (prepared from 2.16 g sodium, 75 ml of absolute ethanol and 150 ml of DME) is dropwise added under stirring. After stirring further 45 minutes at a temperature from −3° to −5° C., it is allowed to reach room temperature which kept on along 8 hours. It is cooled again, then 200 ml of water are dropwise added and the mixture is extracted repeatedly with ethyl acetate; the organic extracts are washed with water, dried and concentrated at vacuum to give an oily residue (16.8 g) which, after purifying through silica-gel column and eluting with methylene chloride-methanol (97:3), allows to isolate 7.12 g (45%) of the nitrile as a white solid, M.P. 100°-103° C. and analysis correct.

IR Spectrum (KBr), cm$^{-1}$: 3100–2800, 2240, 1490, 1240, 1070, 1045, 800, 755.

$^1$H-NMR (CDCl$_3$), ppm: 2.40 and 2.90 (m, A$_2$B$_2$ system; Ar—CH$_2$—CH$_2$—), 4.00 (t, 1H, J=8 Hz; CH—CN), 4.25 (m, 4H; —CH$_2$—CH$_2$O—), 6.7–7.4 (multiple bands, 5H, Ar—, Imidazole) and 7.57 (s, 1H; Imidazole).

EXAMPLE 4

5-[β-(1H-Imidazol-1-yl)ethoxy]-indan-1-carboxylic acid hydrochloride 6.5 g of 1-cyano-5-[β-(1H-imidazol-1-yl)ethoxy]indane and 20 ml of 6N hydrochloric acid are refluxed for 2 hours. The mixture is then allowed to cool at room temperature which causes the hydrochloride to crystallize; after a few hours in refrigerator, it is filtered off, washed with cold 6N HCl and dried, thus yielding 5.9 g (75%) of a white solid, M.P. 169°-171° C. and elemental analysis correct.

IR Spectrum (KBr), cm$^{-1}$: 3300–2400, 1680, 1480, 1265, 1220, 1080, 1040, 820, 735.

hu 1H-NMR (d$_6$-DMSO), ppm: 2.25 and 2.85 (2m, A$_2$B$_2$ system; Ar—CH$_2$—CH$_2$—), 3.85 (t, 1H, J=7 Hz;

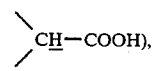

4.37 and 4.55 (2m, A₂B₂ system; —CH₂—CH₂O—), 6.6–7.25 (m, 3H; Ar—), 7.66 and 7.81 (2m, 2H; Imidazole) and 9.22 (s, 1H;

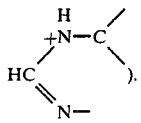

EXAMPLE 5

4-(β-Chloroethoxy)-1-indanone 10.36 g of 4-hydroxy-1-indanone in 340 ml of absolute ethanol are added to a solution of sodium ethoxide in ethanol (prepared from 1.74 g of sodium and 80 ml of absolute ethanol). After 10 min. 20.5 g of β-chloroethyl p-toluenesulphonate in 35 ml of ethanol are dropwise added and the mixture is refluxed under stirring for 24 hours.

Following the steps as described in Ex. 1, 11.95 g of crude product are isolated and after purification through silica-gel column, 8.27 g (56%) of a pure yellowish solid are extracted with methylene chloride. M.P. 56°–58° C. Analysis correct.

IR Spectrum (KBr), cm⁻¹: 3040–2940, 1700, 1475, 1260, 1025, 760.

¹H-NMR (CDCl₃), ppm: 2.62 (m, 2H; —CH₂—CO—), 3.08 (m, 2H; Ar—CH₂—), 3.82 (t, 2H, J=6 Hz; —CH₂—O—), 4.30 (t, 2H, J=6 Hz; —CH₂Cl), 6.88–7.25 (multiple bands, 3H; Ar—).

EXAMPLE 6

4-[β-(1H-Imidazol-1-yl)ethoxy]-1-indanone

To 1.54 g of sodium hydride (55%) in 60 ml of dry N,N-dimethylformamide 2.21 g of imidazole in 15 ml of DMF are added; after 1 hour at 100°–110° C. it is allowed to cool and 6.9 g of 4-(β-chloroethoxy)-1-indanone in 25 ml of DMF are added. The mixture is then heated at 100°–110° C. for 3.5 hours. Following the steps as described in Ex. 2, 5.5 g of crude product are isolated which, after purification through silica-gel column by eluting with methylene chloride:methanol (95:5), allows to isolate 3.8 g (48%) of a white solid. M.P. 132°–134° C. and elemental analysis correct.

IR Spectrum (KBr), cm⁻¹: 3400, 3140–2900, 1700, 1475, 1285, 1260, 1040, 775.

¹H-NMR (CDCl₃), ppm: 2.60 (m, 2H; —CH₂—CO—), 3.00 (m, 2H; Ar—CH₂—), 4.35 (m, 4H; —CH₂—CH₂—O—), 6.75–7.45 (multiple bands, 5H; Ar—, Imidazole) and 7.60 (s, 1H;

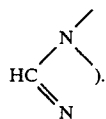

EXAMPLE 7

1-Cyano-4-[β-(1H-imidazol-1-yl)ethoxy]indane

To a solution of 2.68 g 4-[β-(1H-imidazol-1-yl)ethoxy]-1-indanone and 3.3 g of (p-toluenesulfonyl)methylisocyanide in 80 ml of dimethoxyethane, 0.36 g of sodium dissolved in 13.5 of absolute ethanol and 29 ml of dimethoxyethane are added as described in Ex. 3. 2.9 g of crude product are isolated and under purification by silica-gel chromatography allows to isolate 0.86 g (32%) of the nitrile in the form of oil which solidifies along the time (M.P. 115°–117° C.) and is chromatographically pure.

IR Spectrum (KBr), cm⁻¹: 3100–2950, 2220, 1590, 1280, 1080, 780.

¹H-NMR (CDCl₃), ppm: 2.40 and 2.62 (multiplets, A₂B₂ system; Ar—CH₂—CH₂), 4.05 (t, 1H, J=8 Hz; CH—CN), 4.25 (m, 4H; —CH₂—CH₂—O—), 6.6–7.25 (multiple bands, 5H; Ar—, Imidazole) and 7.55 (s, 1H;

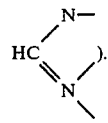

EXAMPLE 8

4-[β-(1H-Imidazol-1-yl)ethoxy]-indan-1-carboxylic acid hydrochloride

To 0.69 g of the nitrile as described in Ex. 7, 3.3 ml of 6N hydrochloric acid are added and subjected to reflux for 2 hours. After cooling, the desired hydrochloride crystallizes; it is then filtered off and dried thus obtaining 0.58 g (69%) of a white solid. M.P. 226°–229° C. and elemental analysis correct.

IR Spectrum (KBr), cm⁻¹: 3400–2500, 1710, 1460, 1285, 1170, 1065, 760.

¹H-NMR (d₆-DMSO), ppm: 2.0–2.8 (2m, A₂B₂ system; Ar—CH₂—CH₂—), 3.95 (t, 1H, J=7 Hz; CH—COOH), 4.4 and 4.6 (2m, A₂B₂ system; —CH₂—CH₂—O—) 6.75–7.25 (m, 3H; Ar), 7.67 and 7.82 (2m, 2H; Imidazole) and 9.27 (s, 1H;

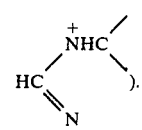

EXAMPLE 9

6-(β-Chloroethoxy)-1-indanone

To a solution of sodium ethoxide in ethanol (prepared from 1.3 g of sodium and 60 ml of absolute ethanol), 7.74 g of 6-hydroxy-1-indanone in 250 ml of ethanol are added. Then 15.3 g of β-chloroethyl p-toluenesulphonate in 25 ml of ethanol are added and the mixture is refluxed under stirring for 24 hours. Following the steps as described in Ex. 1, 8.52 g of crude product are isolated and after purification by silica-gel column 4.5 g (42%) of a solid, chromatographically pure, are isolated with methylene chloride:hexane (9:1). M.P. 76°–80° C. and analysis correct.

IR Spectrum (KBr), cm⁻¹: 3060–2860, 1700, 1480, 1435, 1285, 1040, 1025, 835.

¹H-NMR (CDCl₃), ppm: 2.72 (m, 2H; —CH₂—CO—), 3.07 (m, 2H; Ar—CH₂—), 3.80 (t, 2H, J=6 Hz; —CH₂O—), 4.25 (t, 2H; J=6 Hz; —CH₂Cl), 7.1–7.5 (multiple bands, 3H; Ar—).

EXAMPLE 10

6-[β-(1H-Imidazol-1-yl)ethoxy]-1-indanone

To 0.91 g of sodium hydride (55%) in 40 ml of dry N,N-dimethylformamide 1.31 g of imidazole in 10 ml of DMF are added; after 1 hour at 100°–110° C. the mixture is allowed to cool and 4.09 g of 6-(β-chloroethoxy)-1-indanone in 20 ml of DMF are added. Then the mixture is heated at 100°–110° C. for 3.5 hours. As described in Ex. 2, 3.8 g of crude product are isolated, then purified through silica-gel column by eluting with methylene chloride:methanol (95:5). 1.8 g (40%) of a white solid are obtained with M.P. 120°–122° C. and analysis correct.

IR Spectrum (KBr), cm$^{-1}$: 3100, 3000–2940, 1690, 1485, 1290, 1050, 930, 830, 735.

$^1$H-NMR (CDCl$_3$), ppm: 2.65 (m, 2H; —CH$_2$—CO—), 3.04 (m, 2H; Ar—CH$_2$—), 4.25 (m, 4H; —CH$_2$—CH$_2$—O—), 6.9–7.45 (multiple bands, 5H; Ar—, Imidazole) and 7.58 (s, 1H;

EXAMPLE 11

1-Cyano-6-[β-(1H-imidazolyl-1-yl)ethoxy]indane

To a solution of 2.76 g of 6-[β-(1H-imidazol-1-yl)ethoxy]-1-indanone and 3.42 g of (p-toluenesulfonyl)methylisocyanide in 80 ml of dimethoxyethane, 0.38 g of sodium in 14 ml of absolute ethanol and 30 ml of dimethoxyethane are added according to the steps in Ex. 3. 2.74 g of crude product are isolated and by chromatography 0.92 g (34%) of the nitrile in the form of oil are obtained chromatographically pure.

IR Spectrum (film), cm$^{-1}$: 3100–2930, 2240, 1610, 1490, 1280, 1230, 1080, 820, 740.

$^1$H-NMR (CDCl$_3$), ppm: 2.40 and 2.90 (multiplets, A$_2$B$_2$ system; Ar—CH$_2$—CH$_2$), 4.02 (t, 1H, J=8 Hz; CH—CN), 4.25 (m, 4H; —CH$_2$—CH$_2$—O—), 6.63–7.25 (multiple bands, 5H; Ar—, Imidazole) and 7.56 (s, 1H;

EXAMPLE 12

6-[β-(1H-Imidazol-1-yl)ethoxy]-indan-1-carboxylic acid hydrochloride

To 0.60 g of the nitrile as described in Ex. 11, 2.8 ml of 6N hydrochloric acid are added and refluxed for 2 hours. After cooling, the desired hydrochloride crystallizes; then it is filtered off and dried. 0.45 g (60%) of a white solid are obtained with M.P. 190°–193° C. and elemental analysis correct.

IR Spectrum (KBr), cm$^{-1}$: 3400–2500, 1700, 1460, 1265, 1070, 740.

$^1$H-NMR (d$_6$-DMSO), ppm: 2.1–2.8 (2m, A$_2$B$_2$ system; Ar—CH$_2$—CH$_2$—), 3.92 (t, 1H, J=7 Hz; CH—COOH), 4.4 and 4.60 (2m, A$_2$B$_2$ systems; —CH$_2$—CH$_2$—O—), 6.7 and 7.25 (m, 3H; Ar—), 7.65 and 7.80 (2m, 2H; Imidazole) and 9.25 (s, 1H;

EXAMPLE 13

5-Hydroxy-1-indanone

To a solution of 17.4 g of 5methoxy-1-indanone in 650 ml of dry methylene chloride subject to mechanical stirring 100 g in portions of aluminum bromide are added. After 1 hour at room temperature, the mixture is refluxed for 24 hours and then cooled; thereafter, it is poured onto a mixture containing 260 g of ice and 150 ml of 6N hydrochloric acid under stirring. After 30 minutes, the insoluble is filtered off, washed with water till neutrality and dried, 14.11 g (89%) of a yellow solid chromatographically pure are obtained with M.P. 181°–184° C. and elemental analysis correct.

IR Spectrum (KBr), cm$^{-1}$: 3440, 3100–2900, 1660, 1570, 1300, 1240, 1100, 805.

$^1$H-NMR (d$_6$-DMSO), ppm: 2.50 (m, 2H, —CH$_2$—CO—), 2.95 (m, 2H; Ar—CH$_2$—), 6.75 (m, 2H; Ar—), 7.47 (d, 1H, J=9 Hz; Ar—), and 10.40 (wide, 1H; —OH).

It will be understood that each of the elements described above, or two or more together, may also find a useful application in other types of compositions differing from the types described above.

While the invention has been illustrated and described as embodied in imidazolylethoxyindanes, process for the production thereof and pharmaceutical compositions containing the same, it is not intended to be limited to the details shown, since various modifications and structural changes may be made without departing in any way from the spirit of the present invention.

Without further analysis, the foregoing will so fully reveal the gist of the present invention that others can, by applying current knowledge, readily adapt it for various applications without omitting features that, from the standpoint of prior art, fairly constitute essential characteristics of the generic or specific aspects of the invention.

What is claimed as new and desired to be protected by Letters Patent is set forth in the appended claims.

We claim:

1. Imidazolylethoxyindanes represented by the general formula I:

wherein X is C=O group, a CH—CN group or a CH—COOH group, and the ether group (—O—) is bonded to the indanic group in the 4-, 5- or 6-position thereof, and pharmacologically-acceptable salts thereof.

2. Compound of claim 1 which is 5-[β-(1H-imidazol-1-yl)ethoxy]-1-indanone.

3. Compound of claim 1 which is 1-cyano-5-[β-(1H-imidazol-1-yl)ethoxy]indane.

4. Compound of claim 1 which is 5-[β-(1H-imidazol-1-yl)ethoxy]indan-1-carboxylic acid hydrochloride.

5. Compound of claim 1 which is 4-[β-(1H-imidazol-1-yl)ethoxy]-1-indanone.

6. Compound of claim 1 which is 1-cyano-4-[β-(1H-imidazol-1-yl)ethoxy]indane.

7. Compound of claim 1 which is 4-[β-(1H-imidazol-1-yl)ethoxy]indan-1-carboxylic acid hydrochloride.

8. Compound of claim 1 which is 6-[β-(1H-imidazol-1-yl)ethoxy]-1-indanone.

9. Compound of claim 1 which is 1-cyano-6-[β-(1H-imidazol-1-yl)ethoxy]indane.

10. Compound of claim 1 which is 6-[β-(1H-imidazol-1-yl)ethoxy]indan-1-carboxylic acid hydrochloride.

11. Pharmaceutical compositions useful for the treatment of thrombotic diseases comprising an effective amount of one or more compounds as claimed in claim 1 together with a pharmaceutically-acceptable carrier.

12. Method for the treatment of thrombotic diseases in a subject in need for the same, comprising the step of administering an effective antithrombotic agent of claim 1 to said patient.

* * * * *